(12) United States Patent
Pearce et al.

(10) Patent No.: US 8,349,594 B2
(45) Date of Patent: Jan. 8, 2013

(54) ENZYMATIC OIL INTERESTERIFICATION

(75) Inventors: Steven White Pearce, Durham, NC (US); Lars Saaby Pedersen, Farum (DK); Hans Christian Holm, Hellerup (DK); Tommy Lykke Husum, Hillerod (DK); Per Munk Nielsen, Hillerod (DK)

(73) Assignees: Novozymes A/S, Bagsvaerd (DK); Novozymes North America, Inc., Franklinton, NC (US)

( * ) Notice: Subject to any disclaimer, the term of this patent is extended or adjusted under 35 U.S.C. 154(b) by 787 days.

(21) Appl. No.: 12/064,125

(22) PCT Filed: Sep. 11, 2006

(86) PCT No.: PCT/US2006/035043
§ 371 (c)(1),
(2), (4) Date: Feb. 19, 2008

(87) PCT Pub. No.: WO2007/033013
PCT Pub. Date: Mar. 22, 2007

(65) Prior Publication Data
US 2008/0241897 A1    Oct. 2, 2008

Related U.S. Application Data

(60) Provisional application No. 60/716,231, filed on Sep. 12, 2005.

(51) Int. Cl.
*C12P 7/64* (2006.01)
*C12N 9/20* (2006.01)

(52) U.S. Cl. ............................. 435/134; 435/198
(58) Field of Classification Search ............... None
See application file for complete search history.

(56) References Cited

U.S. PATENT DOCUMENTS

| | | |
|---|---|---|
| 5,128,251 A | 7/1992 | Yokomichi et al. |
| 6,022,577 A | 2/2000 | Chrysam et al. |
| 6,297,279 B1 | 10/2001 | Wang et al. |
| 2005/0014237 A1 | 1/2005 | Lee |
| 2005/0233426 A1 | 10/2005 | Schoerken et al. |

FOREIGN PATENT DOCUMENTS

| | | |
|---|---|---|
| EP | 0 238 023 A2 | 9/1987 |
| GB | 2 179 234 A | 3/1987 |
| JP | 1120295 A | 5/1969 |
| JP | 2203789 A | 8/1990 |
| WO | 03/043972 A2 | 5/2003 |
| WO | WO 2005/003365 | 1/2005 |
| WO | WO 2005/063955 | 7/2005 |
| WO | WO 2006/054183 | 5/2006 |

OTHER PUBLICATIONS

Forssell et al., JAOCS, vol. 69, No. 2, pp. 126-129 (1992).
Knowledge of Lipid Chemistry in Japan, pp. 116-117 (1992).
Hirokawa et al., WPI Accession No. 1995-027258 (1995).
Kato et al., WPI Accession No. 1990-287569 (1990).
Kato et al., WPI Accession No. 1990-287570 (1990).
Berger et al., JAOCS, vol. 62, No. 2, pp. 434-435 (1985).

*Primary Examiner* — Herbert J Lilling
(74) *Attorney, Agent, or Firm* — Kristin J. McNamara

(57) ABSTRACT

The present invention relates to a process for enzymatic lipase interesterification of oils containing a chelating agent by sequential or simultaneous treatment with a base.

15 Claims, 2 Drawing Sheets

ENZYMATIC OIL INTERESTERIFICATION

CROSS-REFERENCE TO RELATED APPLICATIONS

This application is a 35 U.S.C. 371 national application of PCT/US2006/035043 filed Sep. 11, 2006, which claims priority or the benefit under 35 U.S.C. 119 of U.S. provisional application No. 60/716,231 filed Sep. 12, 2005, the contents of which are fully incorporated herein by reference.

FIELD OF THE INVENTION

The present invention relates to an improved process for enzymatic interesterification of oil containing one or more metal chelating agents. The invention also concerns an enzyme composition suitable for lipase interesterification processes.

BACKGROUND OF THE INVENTION

The presence of metals in oils of vegetable or animal origin is known to have deteriorating effect on the stability of these oils. Therefore, oils are often treated with a metal chelating agent, such as citric acid or phosphoric acid, in order to remove such metals.

Often vegetable or animal oils and fats are used as blends in order to show the right physical and chemical properties for a given application. Furthermore the oils or blend of oils have to be further processed in order to obtain suitable properties (e.g., melting profile, mouth feel etc.). The melting profile is often adjusted by rearranging or redistributing the fatty acids on the glycerol backbone either chemically or enzymatically. This process is often referred to as "interesterification". Enzymatic interesterification is carried out using a lipase.

A disadvantage of adding a metal chelating agent to oil is that it has a negative effect on lipase interesterification performance.

SUMMARY OF THE INVENTION

The object of the present invention is to provide improved processes for enzymatic interesterification of oil containing one or more metal chelating agents.

According to the invention interesterification of oil containing one or more metal chelating agents is done by i) contacting the oil with a base and ii) reacting the oil with a lipase.

The invention also relates to an enzyme composition comprising a lipase and a base. Finally the invention relates to use of base for interesterification of oil containing one or more chelating agents.

DETAILED DESCRIPTION OF THE INVENTION

Figure 1:
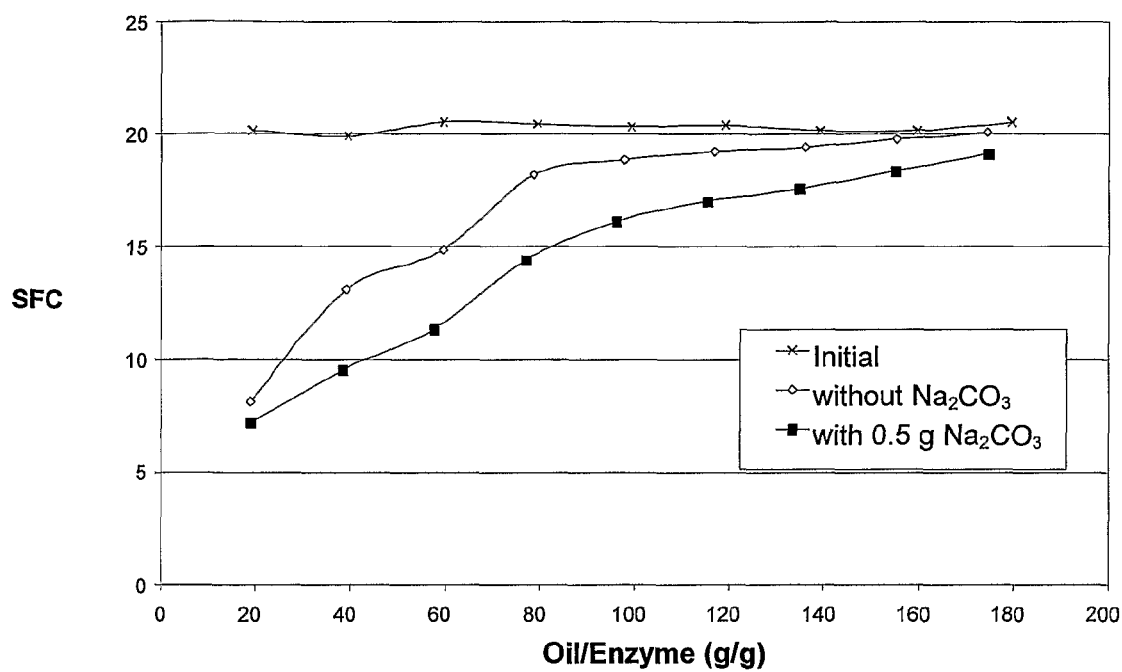
FIG. 1 shows the Solid Fat Content (SFC) at 40° C. of soy oil blend containing citric acid before and after interesterification with and without addition of base.

The main component in vegetable and animal oils and fats are triacylglycerols, also called triglycerides. A triglyceride consists of three fatty acid residues esterified to a glycerol backbone. Partial glycerides may also be present as natural constituents. They may be formed by hydrolysis of one or two fatty acid residues on the glycerol backbone. Vegetable and animal oils and fats often need some modification for making them suitable as food ingredients.

The melting profile often needs to be adjusted in order to give the fat suitable physical properties for a given application. The desired melting profile is dependent on the desired application. The right melting profile is often obtained by a combination of different raw materials and modifications. Vegetable oils typically have a solid fat content (SFC) around 10-30% at 40° C. "SFC" is defined as the percentage of a fat or oil that exists in crystalline form at a given temperature. To be suitable as food ingredient it is in general desired to modify oils to have a SFC at 40° C. in the range from 1 to 10%. For product, such as margarines, the desired SFC lies around 2-4%. However, for other food products, e.g., certain chocolates, a different SFC profile is preferred.

Modification processes comprise blending with other oils, hydrogenation, fractionation and interesterification. Interesterification rearranges the fatty acid residues on the glycerol backbone so that the triglyceride composition is changed. Partial glycerides might also be formed during interesterification, but it is normally not desired. Normally the amounts of partial glycerides formed are small.

Metal ions must be removed carefully from oil as they negatively influence the quality. Even traces of Fe, Cu and Mn are pre-oxidative. In order to sequestering metal ions from oils, one or more metal chelating agents are added. Metal chelating agents, such as preferably citric acid and/or phosphoric acid, are added to oil. After sequestering chelating agent remains dissolved in the oil in concentrations of between 1-100 ppm, typically between 10-90 ppm, such as around 50 ppm. Edible oils are treated with metal chelating agents that are acceptable for the consumer of the end product. In a preferred embodiment the metal chelating agent is an acid, preferably citric acid and/or phosphoric acid. According to the present invention interesterification is carried out enzymatically using a lipase on oil having been subjected to a chelating agent in order to remove metal ions.

A major disadvantage of subjecting oil to a chelating agent is that even minor amounts of chelating agent remaining in the oil has a negative impact on the interesterification performance of lipase. For instance, the inventors observed that the interesterification performance of immobilized *Thermomyces lanuginosa* lipase on soybean oil containing 50 ppm citric acid was as much as 65% lower than on oil without citric acid.

Thus, a problem to be solved is to provide improved processes for enzymatic lipase interesterification of oil comprising one or more metal chelating agents. The improvement includes increased productivity and/or increased average space time yield of the enzyme composition.

The inventors have surprisingly found that adding a base to the oil has a significant positive impact on lipase performance. This is illustrated in the Example 1 below. A process of the invention may be carried out as a traditional lipase interesterification process, except that an effective amount of base is introduced. For instance an interesterification process of the invention may be carried out at a temperature between 50° C. and 100° C., preferably between 60° C. and 90° C., especially from 65° C. to 80° C.

Thus, in the first aspect the invention relates to a process of interesterifying oil containing one or more metal chelating agents comprising the steps of:
  i) contacting said oil with a base,
  ii) reacting the oil with a lipase.

According to the invention steps i) and ii) may be carried out sequentially or simultaneously. Sequential treatment means that oil is pre-treated with base before lipase is added. It is also contemplated according to the invention to add base and a portion, e.g., 10-90%, such as 30-70%, of the lipase initially to the oil and then after a period of time to add the rest of the lipase, e.g., 90-10%, such as 70-30%.

Simultaneous treatment means that oil is treated with base and lipase at the same time. If carrying out steps 1) and 2) simultaneously it may be done by adding a composition of the invention comprising a base and a lipase, preferably immobilized lipase, to the oil. Simultaneous and sequential processes are illustrated in Example 2.

In a preferred embodiment the base is added to the oil before lipase and therefore before interesterification. The base may be added to the oil using any means. In one embodiment the base is incorporated into the oil using a high to low shear mixer. However, other means of mixing are also contemplated. After base is incorporated into the oil, lipase may be introduced.

In another preferred embodiment base is added to the oil simultaneously with the lipase. Base and lipase may be incorporated into the oil in any suitable way such as using a mixer as described above. As will be described further below the base may also advantageously be incorporated into an enzyme composition, e.g., in form of physical mix of lipase, preferably immobilized lipase, and base or as an immobilized lipase with the base incorporated.

In a third preferred embodiment oil is treated with base in a separate process step and the base is removed from the oil, before the oil and enzyme is brought in contact.

In a fourth preferred embodiment the base is packed in a column. The oil is contacted with the base by passing it through packed bed of base inside the column. In this way the base treatment can easily be implemented in, e.g., a typical continuous enzymatic interesterification plant operating with one or more packed bed reactors in series holding lipase.

Without being limited to any theory it is believed that the reason for loss of lipase performance during interesterification of oil containing a metal chelating agent may be that the metal chelating agent, e.g., citric acid, in the local environment around the active site of the enzyme, might affect the charges in an unfavorable way for the lipase, e.g., *Thermomyces lanuginose* lipase. Thus, having base present in the oil changes the charge of acid, e.g., the citric acid, so that it will not affect the lipase adversely, thereby improving the lipase performance.

Edible Oils:

Any edible oil may be used in a process of the invention. The oil may be of any quality such as crude, refined, bleached and deodorized or combinations of these.

For instance, refined oil may be prepared by treating with 0.05-0.1% phosphoric acid to remove gums at a temperature of 60-90° C. for 10-30 minutes. Bleached oil may be prepared by degumming with 0.05-0.1% phosphoric acid, followed by bleaching with 1% of bleaching earth at 105-110° C. for 15-30 minutes and filtration to remove the bleaching earth. Activated bleaching earth may be processed with sulfuric or hydrochloric acid. In another preferred embodiment the oil blend is, e.g., 27%, fully hydrogenated soy oil ("Soy Flakes") blended into soy oil.

In a preferred embodiment the oil is vegetable oil. Examples of vegetable oils include oils selected from the group consisting of Canola oil (rape seed), soybean oil, cotton seed oil, palm oil, palm stearin, palm olein, palm kernel oil, coconut oil, corn oil and sunflower oil.

Also blends of oils are contemplated according to the invention. For instance, oil blends may contain one or more fully as well as partially hardened oils.

In an embodiment the blend is fully or partially hardened soy and/or cottonseed oil in soy oil in a weight based blend ratio of 10:90 to 50:50, preferably 25:75 to 30:70. In a preferred embodiment of the invention the oil blend is a mixture of palm stearin and coconut oil where the coconut oil is either refined or refined and bleached.

In one embodiment the oil to be interesterified is plain palm olein, which gets harder (instead of softer) when interesterified.

Lipases

A lipase, used in a process and/or contained in a composition of the invention, may be obtained from a microorganism, preferably a filamentous fungus, yeast, or a bacterium. In one embodiment the lipase may be formulated as an immobilized product as will be described further below.

For the purpose of the present invention the term "obtained from", as used herein in connection with a specific microbial source, means that the enzyme and consequently the DNA sequence encoding said enzyme is produced by the specific source. The enzyme is then obtained from said specific source by standard known methods enabling the skilled person to obtain a sample comprising the enzyme and capable of being used in a process of the invention. Said standard methods may be direct purification from said specific source or cloning of a DNA sequence encoding the enzyme followed by recombinant expression either in the same source (homologous recombinant expression) or in a different source (heterologous recombinant expression).

The lipase may be a non-specific lipase capable of releasing or binding any fatty acid group from or to any glyceride position. Such lipases have been obtained from *Candida cylindracae, Corynebacterium acnes* and *Staphylococcus aureus* (Macrae, *J.A.O.C.S.*, 1983, 60:243A-246A; U.S. Pat. No. 5,128,251). The lipase may also be of the type that only adds or removes specific fatty acid groups to or from specific glycerides. Such lipases are useful in producing or modifying specific glycerides. Such lipases have been obtained from *Geotrichum candidium* and *Rhizopus, Aspergillus*, and *Mucor* genera (Macrae, 1983; U.S. Pat. No. 5,128,251). The lipase may also be a 1,3 specific lipase. Such lipases have been obtained from *Thermomyces lanuginosa, Rhizomucor miehei, Aspergillus niger, Mucor javanicus, Rhizopus delemar*, and *Rhizopus arrhizus* (Macrae, 1983).

Preferred lipases used in a process of the invention are obtained from a filamentous fungal species within the genus *Thermomyces*, such as a strain of the species *Thermomyces lanuginosa*, preferably the one disclosed in EP Patent No. 305,216-B1, or the genus *Fusarium*, such as a strain of the species *Fusarium culmorum, F. heterosporum, F. solani*, or *F. oxysporum*. In another preferred embodiment the lipase is obtained from yeast, such as Candida, preferably the species *Candida antactica*. Specifically contemplated is lipase B (CalB) from *Candida antactica*.

Immobilized Lipases

Lipases in solid form, such as immobilized lipases, may be used in a process of the invention. Various ways of immobilizing lipases are well known in the art. A review of lipase immobilization is found in "Journal of American Oil Chemist's Society", Vol. 67, pp. 890-910 (1990), where examples of representative lipase immobilizing carriers are illustrated, including inorganic carriers such as diatomaceous earth, silica, porous glass, etc.; various synthetic resins and synthetic resin ion exchangers; and natural polysaccharide carriers such as cellulose and cross-linked dextrin introduced with ion exchange groups.

Suitable carrier substances include polypropylene, e.g., ACCUREL™ (Accordis Membranes GmbH) and silica or mixtures thereof. Suitable immobilization techniques are described in EP 140,542, U.S. Pat. No. 4,818,695, U.S. Pat. No. 5,128,251, U.S. Pat. No. 5,508,185 and U.S. Pat. No. 6,156,548 (which references are all incorporated by reference).

A preferred immobilized *Humicola lanuginose* lipase (same as *Thermomyces lanuginosa* lipase) is described in U.S. Pat. No. 5,776,741 (which is hereby incorporated by reference). Another preferred lipase is *Candida antactica* lipase B (CalB) (see, e.g., Uppeberg et al., 1994, *Structure* 2:293-308) immobilized using the immobilization process described in U.S. Pat. No. 5,776,741.

Finally, examples of suitable commercial available immobilized lipase include the ones sold under the trade names LIPOZYME TL IM™, LIPOZYME RM IM™ (available from Novozymes, Denmark).

Bases

Any base may be used in a process of the invention. In a preferred embodiment the base is a "weak base". A "weak base" is in context of the invention defined as a base that would give a pH of between 8 and 13 if dissolved/dispersed in water at a level of 1 molar, preferably a base that would give a pH of about 11, such as between pH 10 and 12, or corresponding to a pH range of +/−1 around the pH optimum of the lipase in question.

The base may be a strong base including lithium hydroxide (LiOH), sodium hydroxide (NaOH), potassium hydroxide (KOH), rubidium hydroxide (RbOH), cesium hydroxide (CsOH), calcium hydroxide ($Ca(OH)_2$), strontium hydroxide ($Sr(OH)_2$), barium hydroxide ($Ba(OH)_2$).

The base is preferably a base such as an amine or a carbonate. Examples of weak bases may be selected from the group consisting of: ammonia ($NH_3$), alanine ($C_3H_5O_2NH_2$), dimethylamine (($CH_3$)$_2$NH), ethylamine ($C_2H_5NH_2$), glycine ($C_2H_3O_2NH_2$), hydrazine ($N_2H_4$), methylamine ($CH_3NH_2$), trimethylamine (($CH_3$)$_3$N) and sodium carbonate ($Na_2CO_3$), Sodium hydrogen carbonate, ($NaHCO_3$), Sodium nitrite ($NaNO_2$), sodium acetate ($CH_3COO\ Na$).

In a preferred embodiment the base is sodium carbonate ($Na_2CO_3$). In a preferred embodiment the base is used in an amount of 0.01 to 100 milli moles per gram enzyme, more especially, between 0.1 and 60 milli moles of base per gram enzyme.

In an embodiment the base is used in an amount of 0.001 to 100 milli moles per kilo gram of oil, preferably between 0.01 and 10 milli moles of base per kilo gram oil, especially 0.1-1 milli moles per kilo gram of oil.

Enzyme Composition

In this aspect the invention relates to an enzyme composition comprising lipase and base. The base may be any of the ones listed and/or defined in the "Bases"-section above. The enzyme composition may be added directly to the oil containing a chelating agent. An enzyme composition of the invention provides more optimal conditions for the lipase during interesterification of oil comprising a chelating agent than an enzyme composition comprising only a lipase.

The composition of the invention may be formulated in any way suitable for use in interesterification of oil processes. The composition may be formulated as an immobilized product. In a preferred embodiment the composition is a granulate, comprising a lipase and a base. The enzyme composition of the invention may be a mix of immobilized lipase and base or an immobilized lipase having the base incorporated.

The lipase may be any lipase such as the ones described in the "Lipases"-section above. In a preferred embodiment the lipase is derived from *Thermomyces lanuginose* or may be lipase B (CalB) derived from *Candida antactica*. In a preferred embodiment the enzyme composition is a granulate comprising immobilized *Thermomyces lanuginose* lipase or *Candida antactica* lipase B and a base, preferably a weak base, especially sodium carbonate.

Use of Bases

The invention also relates to the use of base in a lipase interesterification process of oil comprising to one or more chelating agents. When base is used in such interesterification process the productivity is increased as illustrated in Example 3. The base and lipase, respectively, may be any of the ones mentioned above in the "Bases" and "Lipases"-sections.

Materials and Methods

Materials:

Enzyme:

Immobilized Lipase A: Immobilized lipase derived from *Humicola lanuginosa/Thermomyces lanuginose* disclosed and produced recombinantly in *Aspergillus oryzae* as disclosed in EP Patent No. 305,216-B1. Immobilization method is described in U.S. Pat. No. 5,776,741.

$Na_2CO_3$: Sigma chemical Company, Analytical grade (Example 2)

$Na_2CO_3$: Sodium Carbonate Anhydrous, NF/EP Fine Granular from Jost Chemical (Example 3)

Oils:

Fully hydrogenated soy oil: ("Soy Flakes" Bunge Foods lot 345M4-T106R3) (Example 1)

Soy oil: "Master Chef Salad Oil" C&T Refinery, Charlotte, N.C. Lot L3C27 1337 (Example 1)

Blend of fully hydrogenated soy bean oil and soy bean oil (Blend ratio 27:73 (w/w)). The liquid soy bean oil is "raffinert soyaolje" from Denofa, Norway. This oil is RBD oil, which is known to contain citric acid. The fully hydrogenated soy bean flakes are from Loders Croklaan, USA. No information on citric acid content of the flakes is available. (Example 2)

Refined blended Palm Stearine and Coconut Oil (Example 3)

Bleached blended Palm Stearine and Coconut Oil (Example 3)

Methods:

Determination of Solid Fat Content (SFC)

The method is used for determination of solid fat content is based on the AOCS Official Method Cd 16b-93 "Solid Fat Content (SFC) by Low-Resolution Nuclear Magnetic Resonance".

Definition of unit: The solid fat content is defined as %

Apparatus: Oven—maintained at 100° C.

Cooling bath set at 0° C.

Constant temperature water baths (10° C. to 60° C.+/−0.1° C.)

Metal blocks (aluminium) with holes for SFC tubes

SFC tubes

NMR spectrometer, Minispec mq-series 2001, Bruker Optics Inc, TX, USA.

Stopwatch

SFC procedure is as follows:

| Step | Action |
|---|---|
| 1 | The fat blend is melted at 100° C. for 30 min (or microwave) |
| 2 | Fat blend (~3 ml) is transfer to NMR tubes(duplicate tubes) |
| 3 | Place the tubes in 100° C. ~5 min (if apparent solids in a tube) |
| 4 | The NMR tubes are transferred to water bath at 60° C. for 5 to 15 min. |
| 5 | The NMR tubes are transferred to Cooling bath at 0° C. for 60 +/− 1 min |
| 6 | The NMR tubes are subsequently placed in water baths for 30 min at the chosen temperature, e.g., typically run temperatures are 10° C., 21.1° C., 33.3° C., and 40° C. |
| 7 | The NMR tubes are transferred to the cavity of the NMR spectrometer one by one and are measured as quickly as possible. The magnet in the NMR spectrometer is thermo stated at 40° C. |

Mineral oil samples for calibration of the NMR instrument is supplied by Bruker Optics Inc, TX, USA
Calculation: The result will be given as a percentage for example "23.24% SFC
Reference: AOCS Official Method Cd 16b-93 "Solid Fat Content (SFC) by Low-Resolution Nuclear Magnetic Resonance" QMS 2003-22839
Multiple Batch Assay The method is used to determine performance of immobilized lipases for interesterification in Multiple Batch Reactions.

Principle: An oil blend is interesterified in a batch reaction using an immobilized lipase as catalyst. At the end of each batch reaction the oil is decanted from the catalyst which remains in the reactor. Then fresh oil is added to the catalyst and another batch reaction is carried out. The average reaction rate of the enzyme is determined from each batch reaction.

Based on the average reaction rate of the enzyme in a number of consecutive batch reactions with reuse of the enzyme, it is possible to estimate the enzyme deactivation rate as a function of oil volume that has been in contact with the enzyme.

Solid fat content (SFC) is used to quantify the change to the fat properties due to the interesterification.

The Results: Typically the experiments are used to:

Make direct side-by-side comparison of the performance of two or more immobilized enzyme products by looking at plots of either the solid fat content or the average reaction rate constant versus batch number or produced amount of oil per mass of immobilized enzyme.

To estimate the average production rate to a given productivity at constant conversion according to the model described below. The unit of the result is mass of oil interesterified. per mass of immobilized enzyme per time.

| | |
|---|---|
| Batch reactor | Duran Square bottles with pouring ring and screw cap. Capacity 250 ml. |
| Oven with orbital shaker | An oven that can keep the temperature constant at 70° C. +/− 2° C. and which can be equipped with an orbital shaker. Shaking diameter: 25 mm Shaking speed: 300 rpm |

For further details please see Novozymes' Standard Method (346-SM-0010.01) which is available on request from Novozymes A/S, Denmark.

EXAMPLES

Example 1

Impact of Base on Lipase Interesterification Performance in Oil Containing Chelating Agent This experiment was carried out to investigate the effect of adding a base ($Na_2CO_3$) to oil containing citric acid.
Preparing Oil Blend with Citric Acid The experiment was carried out using 27% fully hydrogenated soy oil ("Soy Flakes" Bunge Foods lot 345M4-T106R3) blended into commercial soy oil ("Master Chef Salad Oil" C&T Refinery, Charlotte, N.C. Lot L3C27 1337).

Preparation of oil blend: Heat 73 grams fully hydrogenated soy oil to 70-80° C. and add 27 grams soy flakes. Mix and heat until all solids have melted. Add citric acid (10-30 ppm) and stir for about 30 minutes. Fill in plastic bottles and store in freezer until use.
Interesterification of Oil Blend 0.5 gram sodium carbonate ("sodium carbonate, anhydrous, analytical reagent, granular" Mallincrodt catalog number 7525) was poured into 110 gram oil blend together with 0.5 gram immobilized Lipase A. Base and enzyme were allowed to settle by gravity. The oil blend was shaken in an orbital incubator at 200 rpm (25 mm orbit) for about 22 to 23 hours. Interesterification was run at 70° C. and repeated on oil blend prepared without addition of base.
SFC Determination of Interesterified Oil Blend With and Without Base 100 g oil blend was decanted out of the bottle taking care that all enzyme and base is retained in the bottle. The SFC of the oil was determined using the SFC method described earlier. The SFC was measured at 40° C. 100 g fresh oil blend was added to the bottle containing the enzyme and the base and the interesterification procedure was repeated. In total the interesterification was repeated nine times over a period of 2 weeks, using the same enzyme and base while replacing the oil every 22-23 hours. All masses of added and decanted oil were recorded.

The experimental data is displayed in FIG. 1. The solid fat content of the oil after each batch reaction is plotted versus amount of oil that has been in contact with the enzyme. The solid fat content of the oil is lowered due to the interesterification reaction. Hence the lower the SFC obtained at equal reaction conditions, the higher the enzyme activity. It can be seen from FIG. 1 that the presence of base (sodium carbonate) improves the interesterification performance of the lipase significantly.

Example 2

Enhanced Performance of Immobilized Lipase by Pre-Treatment of Oil with Sodium Carbonate The performance of immobilized Lipase A was tested by interesterification in the multiple batch experiments. A blend of fully hydrogenated soy bean oil and soy bean oil (blend ratio 27:73 (w/w)) was used.

In multiple batch reactions, the enzyme is reused in a series of batch reactions. The single batch reaction is carried out with essentially constant oil to enzyme ratio, constant reaction time and a constant temperature of 70° C. The level of interesterification is quantified by measuring the solid fat content (SFC) of the fat at 40° C.

The batch reactor is a 250 ml square shaped bottle. During the reaction the bottle is continuously shaken in an orbital shaker. The orbital diameter is 1 inch and the shaker is orbiting at 200 rpm.

A batch of immobilized Lipase A (batch LA350005) and sodium carbonate ($Na_2CO_3$) was tested by 1) $Na_2CO_3$ pre-treatment of the oil prior to interesterification, i.e., sequential treatment, and 2) $Na_2CO_3$ treatment of the oil during the interesterification, i.e., simultaneous treatment. Reference interesterification experiments with the immobilized Lipase A were carried out using the same oil blend, but without pre-treatment of the oil. Three combinations of pre-treatment and enzyme were tested.

Pretreatment

Pre-treatment of oil was carried out according to the following procedure. A sealed container filled with untreated oil was placed overnight in a heating cabinet at 70° C.

The oil was then poured into 1 liter bottles and 1% (w/w) of sodium carbonate was added. The bottle was flushed with nitrogen and firmly closed. The bottle with oil and sodium carbonates was placed on a water bath overnight. The oil and sodium carbonate was constantly mixed using a magnetic stirring bar. Next day the stirring was stopped in order to let the sodium carbonate sediment. For the multiple batch experiments the oil was decanted directly from this flask taking care that the pre-treatment chemical remained in the bottle.

Simultaneous

For the simultaneous treatment, the enzyme and the sodium carbonate was weighted directly into the reaction bottle. 1 gram of sodium carbonate and 0.5 gram of immobilized Lipase A were added to the bottle. The solid pre-treatment component remained in the bottle throughout the whole experiment.

100 gram oil was contacted with 0.5 gram Lipase A.

Activity Calculation

The kinetics for the interesterification reaction of Lipase A is modeled using a first order reversible reaction model with solid fat content as the concentration parameter.

$$k = \frac{M_b}{w \cdot t_b} \cdot \ln\left[\frac{SFC_{in} - SFC_{eq}}{SFC_{out} - SFC_{eq}}\right] \quad (1)$$

where
k is the rate constant,
$SFC_{in}$ is the solid fat content of the oil that enters the reactor,
$SFC_{out}$ is the solid fat content of the oil that leaves the reactor,
$SFC_{eq}$ is the solid fat content of the oil at the reaction equilibrium,
w is the mass of the catalyst—immobilized Lipase A,
$M_b$ is the mass of oil in the reactor, and
$t_b$ is the reaction time in the batch reactor.

An exponential model can be used, to describe the rate constant as a function of the productivity $$k_{model} = k_0 \cdot \exp\left(\frac{-\ln(2)}{V_{1/2}} \cdot V\right) \quad (2)$$

where
$k_{model}$ is the model of the rate constant
$k_0$ is the rate constant for the fresh enzyme $V_{1/2}$ is the volume based half life of the enzyme—the amount of oil per amount of enzyme that is needed to reduce $k_{model}$ by 50%.

V is the amount of oil per amount of enzyme that has passed the reactor.

Figure 2:
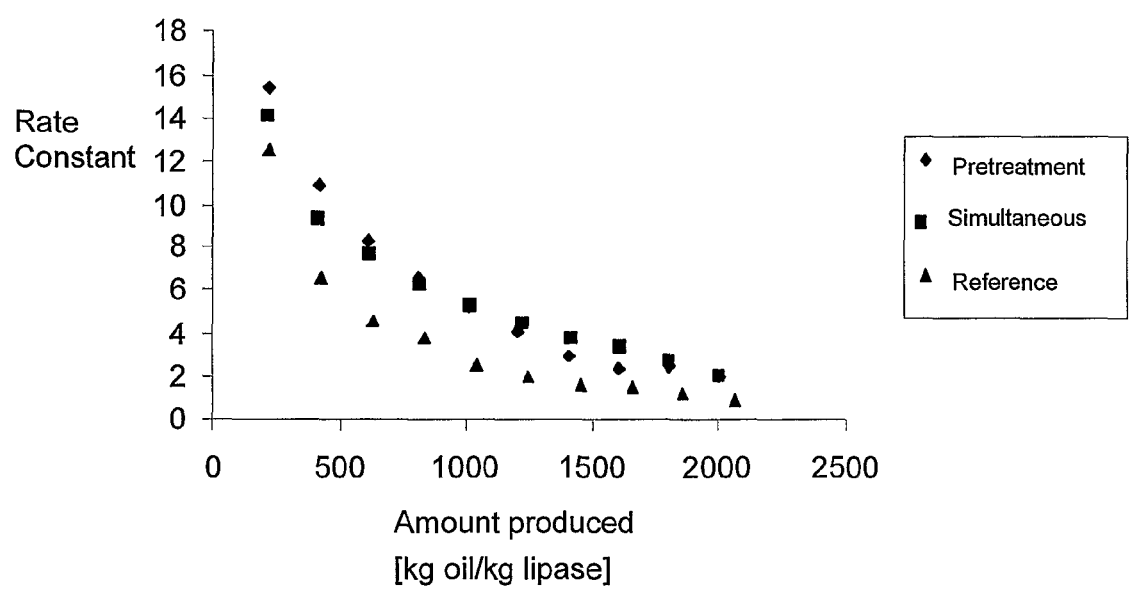
FIG. 2 shows the rate constant (1/hr) vs. amount of oil produced for immobilized Lipase A (batch LA350005). Pre-treatment: Data from the process where the oil is pre-treated with sodium carbonate. Simultaneous: Data from the process where the oil is sodium carbonate treated and interesterified simultaneously. Reference (Control): Data from interesterification of oil without pre-treatment.

In FIG. 2 the rate constant is plotted versus amount of oil interesterified per amount of immobilized Lipase A for each of the treatments.

From FIG. 2 it can be seen that the enzyme maintains significantly higher activity in the oil that has been either pre-treated or treated with sodium carbonate during interesterification.

By fitting the inactivation model given in (2) above to the data shown in FIG. 2, the rate constant for fresh enzyme and the volume based half-life is determined. These numbers are listed in Table 1 below.

TABLE 1

Model parameters - Lipozyme TL IM, batch LA350005.

| Sample Id. Compound | Sequence | $V_{1/2}$ [kg/kg] | $k_0$ [$min^{-1}$] |
|---|---|---|---|
| $Na_2CO_3$ | Pretreated | 596 | 0.293 |
| $Na_2CO_3$ | Pretreated | 594 | 0.301 |
| $Na_2CO_3$ | Pretreated | 626 | 0.289 |
| $Na_2CO_3$ | Simultaneous | 722 | 0.247 |
| $Na_2CO_3$ | Simultaneous | 788 | 0.235 |
| None | Reference | 504 | 0.215 |
| None | Reference | 418 | 0.237 |
| None | Reference | 414 | 0.250 |

$k_0$ is the rate constant for fresh enzyme and $V_{1/2}$ the volume based half life.

The parameters determined for the inactivation model indicate that it is mainly the stability of the enzyme in the oil, represented by the volume based half-life that is increase by the sodium carbonate treatment. The volume based half-life is increased by 30-70% by sodium carbonate treatment.

Example 3

The Productivity Achievable with Lipase A, Measured by MBA (Multiple Batch Assay) of the Oil Enzyme Combination In this experiment the interesterification productivity was tested using the MBA (multiple batch assay) described in the "Materials & Methods" section above. Oil blends were mixtures of palm stearin and coconut oil where the coconut oil was either refined or refined and bleached. These blends were pretreated with $Na_2CO_3$ and interesterified with immobilized Lipase A and the productivity of the enzyme in the oil was compared to references that were not $Na_2CO_3$ pretreated.

TABLE

Summary of Productivity Results

| Sample | | | Productivity kg oil/kg enzyme 10% relative lipase activity left when productivity tested |
|---|---|---|---|
| Refined Oil | None | Reference | 1,650 |
| | $Na_2CO_3$ | Pretreated | 3,620 |
| Bleached Oil | None | Reference | 210 |
| | $Na_2CO_3$ | Pretreated | 3,250 |

The productivity of the refined oil sample was found to be 1,650 kg oil/kg enzyme. When pretreated with $Na_2CO_3$ the productivity increased to 3,620 kg oil/kg enzyme.

The bleached oil gave a productivity value of 210 kg oil/kg enzyme. When bleached oil was pretreated with $Na_2CO_3$ the productivity increased to 3,250 kg oil/kg enzyme whereas the productivity of the refined oil increased from 1,650 to 3,620 kg oil/kg enzyme.

The invention claimed is:

1. A process of interesterifying oil containing one or more citric acid and/or a phosphoric acid metal chelating agents comprising the steps of:
   a) contacting an oil with a base, and
   b) reacting the oil with a lipase, wherein steps a) and b) are carried out sequentially or simultaneously.

2. The process of claim 1, wherein the oil is a blend of two or more oils.

3. The process of claim 1, wherein the oil is an edible oil.

4. The process of claim 1, wherein the oil is vegetable oil.

5. The process of claim 4, wherein the vegetable oil is selected from the group consisting of palm stearin, palm olein, palm kernel oil, corn oil, Canola oil (rape seed), soybean oil, cotton seed oil, palm oil, coconut oil, or sunflower oil, or a blend thereof.

6. The process of claim 1, wherein the oil is crude, refined, bleached, deodorized or a combination thereof.

7. The process of claim 1, wherein the metal chelating agent is present in the oil in a concentration of between 1 to 100 ppm.

8. The process of claim 1, wherein the base is sodium hydroxide.

9. The process of claim 1, wherein the base is a weak base.

10. The process of claim 1, wherein the lipase is a 1,3-specific lipase.

11. The process of claim 1, wherein the lipase is a fungal lipase of the genus *Thermomyces*.

12. The process of claim 1, wherein the lipase is immobilized.

13. The process of claim 1, wherein the base is used in an amount of 0.001 to 100 millimoles per kilo gram of oil.

14. The process of claim 1, wherein the temperature during interesterification is between 50° C. and 100° C.

15. A process of interesterifying oil comprising
   contacting an oil with citric acid and/or phosphoric acid;
   contacting the oil with a base; and
   reacting the oil with a lipase.

* * * * *